US00PP14292P39

(12) United States Plant Patent
Yomo

(10) Patent No.: US PP14,292 P3
(45) Date of Patent: Nov. 11, 2003

(54) VERBENA PLANT NAMED 'SUNMARICOS'

(50) Latin Name: *Verbena hybrida*
Varietal Denomination: Sunmaricos

(75) Inventor: Yasunori Yomo, Yasu-gun (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/066,655

(22) Filed: Feb. 6, 2002

(65) Prior Publication Data

US 2003/0150037 P1 Aug. 7, 2003

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | |
|---|---|---|---|
| PP8,995 | P | 11/1994 | Tachibana et al. |
| PP9,014 | P | 12/1994 | Tachibana et al. |
| PP9,059 | P | 2/1995 | Tachibana et al. |
| PP9,085 | P | 3/1995 | Tachibana et al. |
| PP9,121 | P | 4/1995 | Tachibana et al. |
| PP9,411 | P | 12/1995 | Tachibana et al. |
| PP10,311 | P | 3/1998 | Tachibana |
| PP10,705 | P | 11/1998 | Tachibana |
| PP10,743 | P | 1/1999 | Nagase |
| PP10,755 | P | 1/1999 | Nagase |
| PP10,801 | P | 2/1999 | Nagase |
| PP11,037 | P | 8/1999 | Yomo et al. |
| PP11,104 | P | 10/1999 | Yomo et al. |
| PP11,113 | P | 11/1999 | Yomo et al. |
| PP11,120 | P | 11/1999 | Yomo et al. |
| PP11,130 | P | 11/1999 | Yomo et al. |

*Primary Examiner*—Kent Bell
(74) *Attorney, Agent, or Firm*—Burns, Doane, Swecker & Mathis, L.L.P.

(57) ABSTRACT

Disclosed herein is a new and distinct variety of Verbena plant having a spreading growth habit and long stems. The plant forms flowers in clusters with a great profusion of blooms. The blooming period commonly is from late April to November and the flowering duration is long. Accordingly, the entire plant remains in bloom for an extended period of time. The flower size is large and the petal color of the flowers is deep purplish pink. The plant is highly tolerant to heat, and exhibits a high resistance to pests and diseases, particularly powdery mildew, and has a high resistance to rain.

2 Drawing Sheets

Botanical/commercial classification: Verbena hybrida/ Verbena Plant.
Varietal denomination: cv. 'Sunmaricos'.

BACKGROUND OF THE VARIETY

The present invention provides a new and distinct variety of *Verbena×hybrida* plant obtained from the open-pollination of the '114-7' variety (non-patented in the United States). The identity of the male parent is unknown. The '114-7' variety was developed from crossing a *Verbena hybrida* plant named 'Amethyst' (non-patented in the United States) as female and an unnamed and non-patented wild type of *Verbena peruviana* plant native to Brazil as male.

The Verbena is a very popular plant and is used for flower bedding and potting in the summer season. There are only a few varieties of Verbena plants which have a spreading growth habit, abundant branching, many flowers in a cluster, and a high resistance to rain, heat, cold and diseases. Accordingly, this invention is aimed at obtaining a new variety having a spreading growth habit, abundant branching, a large number of deep purplish pink flowers in a cluster having a large diameter, and a high tolerance to heat and cold, and resistance to diseases and pests.

In August 1997, seedlings resulting from open-pollination of the '114-7' variety were obtained at Torihara, Hakushu-cho, Kitakoma-gun, Yamanashi-ken, Japan. In January 1998, a seedling was selected in view of its spreading growth habit, less bluish and more reddish pigment in the flower than its parent and deep purplish pink petals. Such selection was propagated by the use of cuttings, and was evaluated in flowerbeds and planters beginning in April 1998 at Torihara, Hakushu-cho, Kitakoma-gun, Yamanashi-ken, Japan, and at Aza-Iketani, Omori-cho, Yokaichi-shi, Shiga-ken, Japan. The botanical characteristics of the plant were examined using the similar varieties 'SUNVP-PI' (U.S. Plant Pat. No. 10,705) and 'Surimarisa' (U.S. Plant Pat. No. 11,130) for comparison. As a result, it was concluded that the subject Verbena plant is distinguishable from other varieties whose existence is known to me and is uniform and stable in its characteristics. This new variety was named 'Sunmaricos'.

In the following description, the color-coding is in accordance with The R.H.S. Colour Chart of The Royal Horticultural Society, London, England. A color chart based on The Japan Color Standard for Horticultural Plant (J.H.S. Color Chart) is also added for reference.

The main botanical characteristics of the parent '114-7' variety are as follows:

Plant:
- *Growth habit.*—Spreading.
- *Plant height.*—Approximately 15–20 cm.
- *Plant extension.*—Approximately 60–100 cm.

Stem:
- *Diameter.*—Approximately 1.5–2.5 mm.
- *Anthocyanin pigmentation.*—Present.
- *Branching.*—Abundant.
- *Pubescence.*—Medium.
- *Length of internodes.*—Approximately 2.5–4.5 cm.

Leaf:
*Phyllotaxis.*—Opposite.
*Shape of blade.*—Hastate.
*Length.*—Approximately 3.0–4.5 cm.
*Width.*—Approximately 2.0–2.5 cm.
*Depth of incision.*—Shallow.
*Color.*—Dark olive green (R.H.S. 137B, J.H.S. 3707).
*Pubescence.*—Sparse.
Flower:
*Facing direction.*—Upward.
*Outward curvature of petal.*—Flat.
*Diameter.*—Approximately 1.5–2.0 cm.
*Height.*—Approximately 2.0–2.5 cm.
*Color.*—Vivid purple (R.H.S. 88A, J.H.S. 8606).
*Color presentation.*—Uneven.
*Overlapping of petals.*—Separated petals.
*Shape of cluster.*—Obconical.
*Length of cluster.*—Approximately 3.0–5.0 cm.
*Diameter of cluster.*—Approximately 4.0–5.5 cm.
*Calyx.*—Approximately 1.2–1.4 cm in length.
*Anthocyanin pigmentation of calyx limb.*—Present.
*Peduncle.*—Approximately 1.0–2.0 mm in thickness, and approximately 2.0–4.5 cm in length.
*Number of flowers.*—Many (approximately 11–14).
*Reproductive organs.*—1 pistil and 4 stamens.
*Flower fragrance.*—Absent.
*Flowering duration.*—Long.
Physiological and ecological characteristics: High resistance to diseases and pests and high tolerance to heat and cold.

The main botanical characteristics of the 'SUNVP-PI' variety are as follows:

Plant:
*Growth habit.*—Spreading.
*Plant height.*—Approximately 15–25 cm.
*Plant width.*—Approximately 50–70 cm.
*Growth.*—Very vigorous with abundant branching and a great profusion of blooms with the entire plant remaining in bloom for a considerable period of time.
Stem:
*Diameter.*—Approximately 2.0–3.0 mm.
*Anthocyanin pigmentation.*—Present.
*Branching.*—Abundant.
*Pubescence.*—Medium.
*Length of internode.*—Approximately 4.0–5.0 cm.
Leaf:
*Phyllotaxis.*—Opposite.
*Shape of blade.*—Hastate.
*Length.*—Approximately 4.0–5.0 cm.
*Width.*—Approximately 2.0–2.5 cm.
*Depth of incision.*—Shallow.
*Color.*—Grayish olive green (R.H.S. 137A–137B, J.H.S. 3716).
*Pubescence.*—Sparse.
Flower:
*Facing direction.*—Upward.
*Outward curvature of petal.*—Curved.
*Diameter.*—Approximately 1.5–2.0 cm.
*Height.*—Approximately 20 mm.
*Color.*—Deep purplish pink (R.H.S. 70C, J.H.S. 9213).
*Overlapping of petals.*—Separate petals.
*Spike.*—Aproximately 30–35 mm in length, and approximately 50–55 mm in diameter.
*Calyx.*—Approximately 1.0 cm in length.
*Anthocyanin pigmentation of calyx limb.*—Present.
*Peduncle.*—Approximately 2–3 mm in thickness, and approximately 5.0–6.0 cm in length.
*Number of flowers.*—Plentiful (approximately 13–15).
*Reproductive organs.*—1 pistil and 5 stamens.
*Flower fragrance.*—Absent.
*Flowering duration.*—Long.
Physiological and ecological characteristics: High resistance to diseases and pests, particularly powdery mildew. High tolerance to heat and moderate tolerance to cold.

The main botanical characteristics of 'Sunmarisa' variety are as follows:

*Growth habit.*—Spreading.
*Plant width.*—Approximately 65–71 cm.
*Plant height.*—Approximately 8–9 cm.
Stem:
*Diameter.*—Approximately 1.7–2.2 mm.
*Anthocyanin pigmentation.*—Absent.
*Pubescence.*—Medium.
*Branching.*—Medium.
*Length of internode.*—Medium, approximately 1.7–2.7 cm.
Leaf:
*Phyllotaxis.*—Opposite.
*Shape of blade.*—Oblong-lanceolate.
*Depth of blade incision.*—Shallow.
*Length.*—Medium, approximately 2.9–3.6 cm.
*Width.*—Medium, approximately 1.6–2.4 cm.
*Color.*—Dark olive green (R.H.S. 146A, J.H.S. 3707).
*Pubescence.*—Slight.
*Petiole.*—Present.
*Diameter of petiole.*—Approximately 1.0–1.2 mm.
*Length of petiole.*—Approximately 1.2–2.5 mm.
Flower:
*Shape of cluster.*—Obovate.
*Length of cluster.*—Approximately 23–44 mm.
*Diameter of cluster.*—Approximately 40–58 mm.
*Facing direction.*—Upward.
*Outward curvature of petal.*—Slightly curved.
*Diameter.*—Approximately 1.8–1.9 cm.
*Height.*—Approximately 2.1–2.2 cm.
*Color.*—Light purplish pink (R.H.S. 62C, J.H.S. 9503).
*Eye color.*—Pale yellow (R.H.S. 11D, J.H.S. 2503).
*Eye size.*—Small.
*Color presentation.*—Substantially even.
*Overlapping of petals.*—Separate petals.
*Incision of petal.*—Present.
*Number of petals.*—5.
*Sepals.*—Tubular in configuration.
*Length of calyx.*—Approximately 1.2–1.4 cm.
*Anthocyanin pimentation of calyx limb.*—Absent.
*Color of anther.*—Yellow green.
*Diameter of peduncle.*—Approximately 0.9–1.4 mm.
*Length of peduncle.*—Approximately 19–45 mm.
*Color of peduncle.*—Strong yellow green (R.H.S. 144A, J.H.S. 3507).
*Number of flowers.*—Commonly approximately 13±2.
*Flower bearing.*—In a cluster.
*Reproductive organs.*—1 pistil and 4 stamens.
*Flower fragrance.*—Absent.
*Flowering time.*—Early.
*Flowering duration.*—Long.

*Pollen.*—Brilliant greenish-yellow (R.H.S. 6C, J.H.S. 2704) in coloration.

Physiological and ecological characteristics: High resistance to diseases and pests, particularly powdery mildew. High tolerance to heat and drought, high tolerance to rain, and medium tolerance to cold.

This new 'Sunmaricos' variety was asexually reproduced by the use of cuttings at Youkaichi-shi, Shiga-ken, Japan and the homogeneity and stability thereof were confirmed. The new variety has been found to reproduce true to type in subsequent generations when asexually reproduced.

SUMMARY OF THE VARIETY

This new variety of Verbena plant has a broad spreading growth habit and long stems. The plant is well branched and forms abundant flowers in a cluster. The blooms are present in profusion. The flowering time is early and blooming period is from early April to November and the flowering duration is long. The entire plant remains in bloom for an extended period of time. The flower size is large and the petal coloration of the flowers is deep purplish pink. The plant is highly tolerant to heat, exhibits a high resistance to pests and diseases, particularly powdery mildew, and has a high resistance to rain.

It commonly takes approximately 12 weeks to produce a finished plant of the new variety following the rooting of a cutting.

BRIEF DESCRIPTION OF THE PHOTOGRAPHS

DESCRIPTION OF THE VARIETY

Figure 1:
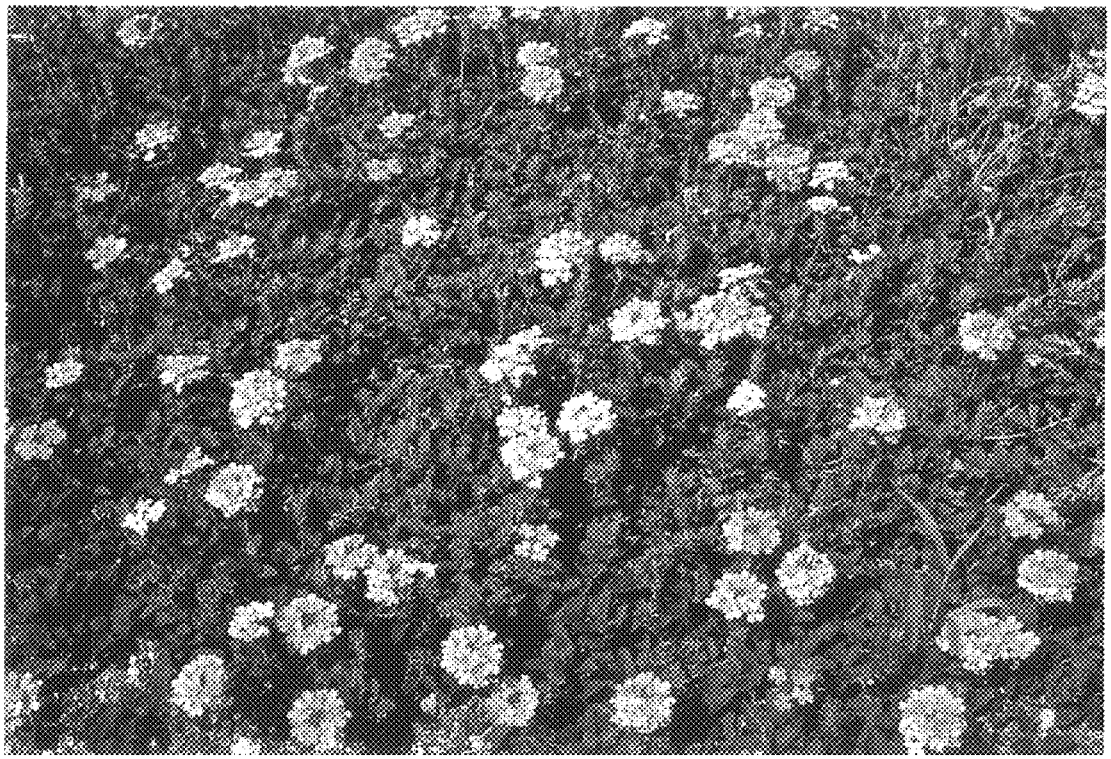
FIG. 1 is a photograph of flowers of the new variety of Verbena plant while growing in the ground. Such plant as well as the other plants described herein was approximately six months of age.
Figure 2:
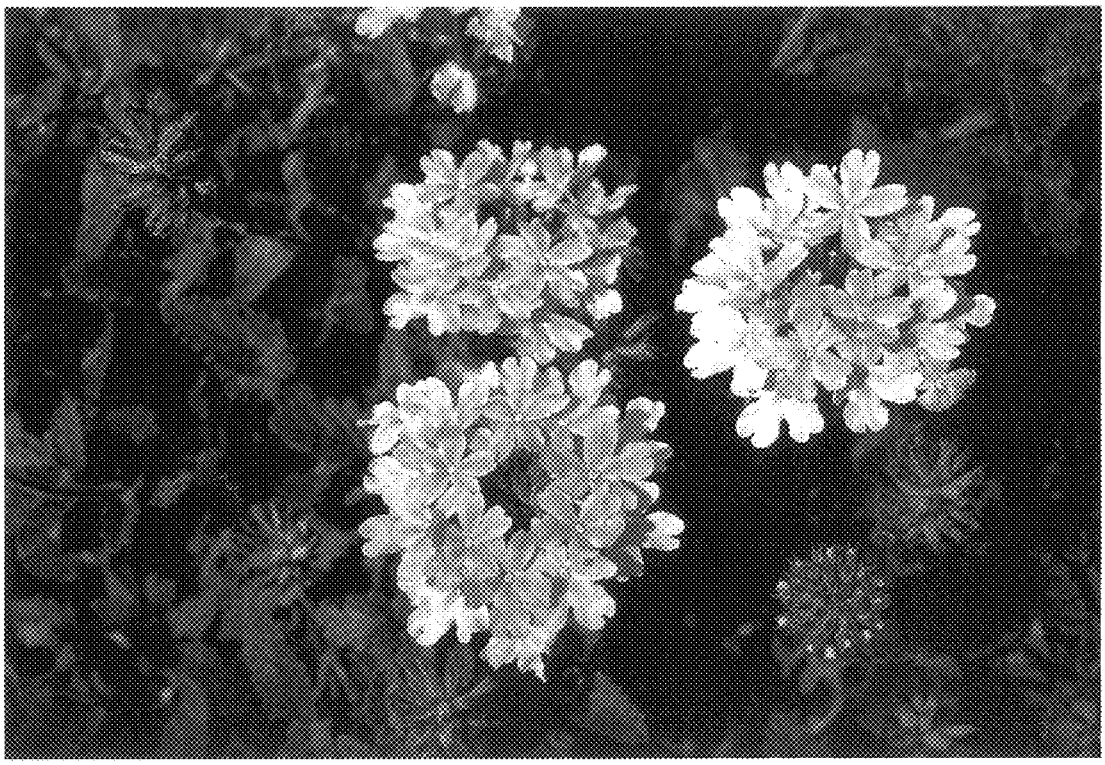
FIG. 2 is a photograph of flowers of the new variety of Verbena plant.

The botanical characteristics of the new and distinct variety of Verbena plant 'Sunmaricos' are presented hereafter. Such plants were being grown in 30 cm pots at Youkaichi-shi, Shiga-ken, Japan.

Plant:
- *Growth habit.*—Spreading.
- *Plant height.*—Approximately 12–15 cm.
- *Plant width.*—Approximately 100–120 cm.

Stem:
- *Diameter.*—Approximately 2.0–2.5 mm.
- *Length.*—Commonly approximately 2.5 to 4.5 cm.
- *Anthocyanin pigmentation.*—Present.
- *Branching.*—Abundant. Each single branch commonly produces two additional branches. More specifically, a single branch commonly becomes three branches and those three branches commonly produce nine branches, etc.
- *Pubescence.*—Medium.
- *Subterranean stem.*—Absent. However, when the stems contact the surface of the soil, the nodes take root in the ground and the plant growth thereby spreads.
- *Length of internodes.*—Approximately 2.5–4.5 cm.

Leaf:
- *Phyllotaxis.*—Opposite.
- *Shape of blade.*—Hastate.
- *Blade margin.*—Serrate.
- *Length.*—Approximately 2.9–3.5 cm.
- *Width.*—Approximately 1.6–2.2 cm.
- *Depth of incision.*—Absent.
- *Leaf apex.*—Acute.
- *Leaf base.*—Rounded.
- *Color.*—Dark olive green (R.H.S. 137B, J.H.S. 3707) on the upper surface, and moderate olive green (R.H.S. 146A and J.H.S. 3508) on the under surface.
- *Venation pattern.*—Dichotomous.
- *Pubescence.*—Medium.
- *Petioie.*—Present.
- *Petiole color.*—Moderate olive green (R.H.S. 137A and J.H.S. 3508).
- *Diameter of petiole.*—Approximately 1.0–1.2 mm.
- *Length of petiole.*—Approximately 1.5–2.0 mm.

Flower:
- *Bud length.*—Approximately 1 to 1.2 cm.
- *Bud diameter.*—Approximately 1.5 to 2 mm.
- *Bud shape.*—Generally tubular.
- *Bud color.*—R.H.S. 141C.
- *Shape of cluster.*—Obconical.
- *Length of cluster.*—Approximately 25–35 mm.
- *Diameter of cluster.*—Approximately 50–60 mm.
- *Facing direction.*—Upward.
- *Outward curvature of petal.*—Flat.
- *Diameter.*—Approximately 1.8–2.2 cm.
- *Length.*—Approximately 1.9–2.1 cm.
- *Color.*—Deep purplish pink (R.H.S. 73A, J.H.S. 9205) on the upper surface, and strong purple (R.H.S. 86B, J.H.S. 8310) on the under surface.
- *Color presentation.*—Some variegation commonly is present at the margin. Such variegation commonly is R.H.S. 73C in coloration.
- *Petal apex.*—Rounded.
- *Petal base.*—Tubular.
- *Petal margin.*—Generally flat and uncurled.
- *Petal texture.*—Generally smooth.
- *Length of calyx.*—Approximately 1.1–1.2 cm.
- *Shape of calyx.*—Possesses one tubular sepal having an acute apex and a rounded base.
- *Color of calyx.*—R.H.S. 138A on the upper surface, and R.H.S. 138B on the under surface.
- *Incision of petal.*—Present in the apex of each petal.
- *Number of petals.*—5.
- *Sepals.*—Tubular in configuration.
- *Anthocyanin pigmentation of calyx limb.*—R.H.S. 60B.
- *Color of anther.*—Pale yellow green. (R.H.S. 1B, J.H.S. 3102).
- *Color of the filament.*—R.H.S. lB.
- *Pollen color.*—Present in a moderate quantity and R.H.S. 1B in coloration.
- *Stigma color.*—R.H.S. 4D.
- *Style color.*—R.H.S. 144B.
- *Ovaries.*—Commonly four in number.
- *Diameter of peduncle.*—Approximately 1.6–2.0 mm.
- *Length of peduncle.*—Approximately 3.3–4.2 mm.
- *Color of peduncle.*—Moderate olive green (R.H.S. 146A and J.H.S. 3508).
- *Number of flowers.*—Medium (approximately 9–14).
- *Flower bearing.*—In a cluster (as illustrated).
- *Reproductive organs.*—1 pistil and 4 stamens.
- *Pollen.*—Brilliant greenish-yellow (R.H.S. 6C, J.H.S. 2704) in coloration.
- *Flower fragrance.*—Absent.

*Flowering time.*—Early.

*Flowering duration.*—Long.

*Flower longevity.*—When planted during March, the plant commonly blossoms from early April to November. A bloom cluster is commonly present for approximately 2 to 3 weeks, and an individual bloom within the cluster commonly lasts for approximately 7 to 10 days on the plant.

Physiological and ecological characteristics: High resistance to diseases and pests, particularly powdery mildew. High tolerance to heat and drought, high tolerance to rain, and medium tolerance to cold. Plants of the new variety have withstood a temperature of 4° F.

This new variety of Verbena plant is most suitable for flower bedding and potting, particularly in planters. It is further excellent for use as a ground cover.

I claim:

1. A new and distinct Verbena plant having the following combination of characteristics:

(a) exhibits a broad spreading growth habit with long stems, (b) forms in abundance clusters of attractive deep purplish pink blossoms that remain on the plant for an extended period of time, and (c) exhibits good tolerance to rain, heat, drought, and diseases;

substantially as herein shown and described.

* * * * *

UNITED STATES PATENT AND TRADEMARK OFFICE

CERTIFICATE OF CORRECTION

PATENT NO. : PP14,292 P3
DATED : November 11, 2003
INVENTOR(S) : Yasunori Yomo

It is certified that error appears in the above-identified patent and that said Letters Patent is hereby corrected as shown below:

Column 2,
Line 7, delete "'Surimarisa'" and insert -- 'Sunmarisa' --.

Signed and Sealed this

Thirty-first Day of August, 2004

JON W. DUDAS
*Director of the United States Patent and Trademark Office*